United States Patent [19]

Fischer

[11] 4,413,199

[45] Nov. 1, 1983

[54] ELECTRICAL TOOTH CLEANER APPARATUS

[75] Inventor: Franz Fischer, Triengen, Switzerland

[73] Assignee: Trisa Bürstenfabrik AG, Triengen, Switzerland

[21] Appl. No.: 207,957

[22] PCT Filed: Feb. 1, 1980

[86] PCT No.: PCT/CH80/00014
§ 371 Date: Oct. 5, 1980
§ 102(e) Date: Aug. 19, 1980

[87] PCT Pub. No.: WO80/01533
PCT Pub. Date: Aug. 7, 1980

[30] Foreign Application Priority Data

Feb. 5, 1979 [DE] Fed. Rep. of Germany ....... 2904327

[51] Int. Cl.³ .................................. H02K 7/14
[52] U.S. Cl. ........................ 310/50; 310/51; 310/91
[58] Field of Search ............ 310/50, 51; 335/199, 335/205; 310/89, 91

[56] References Cited

U.S. PATENT DOCUMENTS

| 3,114,807 | 12/1963 | Koda | 335/199 |
| 3,235,897 | 2/1966 | Fortenberry | 15/24 |
| 3,316,428 | 4/1967 | Hart | 310/51 |
| 3,733,634 | 5/1973 | Golbe | 310/50 |

*Primary Examiner*—Donovan F. Duggan
*Assistant Examiner*—Anita M. Ault
*Attorney, Agent, or Firm*—Werner W. Kleeman

[57] ABSTRACT

A tooth cleaning apparatus having two housing portions is disclosed. Between bot housing portions, which are connected with one another by means of a snap connection, a rubber elastic ring is fixedly clamped. This ring is inserted into a groove at a support element, to which the drive motor is attached as well as a printed circuit board. A magnetically actuable switch is mounted to this circuit board is for turning-on turning-off the motor. This switch is activated by means of a magnetic element, which is secured at an actuation element displaceably mounted at the housing outer surface. The vibration dampening ring prevents transmission of vibrations emanating from the motor to the housing and at the same time serves as sealing element.

15 Claims, 2 Drawing Figures

ELECTRICAL TOOTH CLEANER APPARATUS

BACKGROUND OF THE INVENTION

The present invention relates to an electrical tooth cleaning apparatus, and, more particularly, to an electrical tooth cleaning apparatus in which the drive motor is fixedly held in position in the housing by means of a vibration dampening element.

In the tooth cleaning apparatus known from Swiss Patent No. 425,719, the drive motor is displaceably mounted at the rear housing portion and bears, on the one hand, at the front housing portion and, on the other hand, by means of a compression spring, at the base of the rear housing portion. Under the action of this compression spring, both of the housing portions, held together by a O-ring, are clamped together while compressing the O-ring. This results in a deformation of the O-ring which ensures a watertight closure. With this solution, the joining together of both housing portions is indeed relatively simple. However, certain constructional measures are still required for this purpose, such as the support of the motor at the front housing portion and the provision of a compression spring. These measures result in a more expensive fabrication and require a greater amount of time during assembly.

In U.S. Pat. No. 3,235,897 there is shown a solution wherein the drive motor has a protruding, rigid bead, which is fixedly clamped between both threadable interconnected housing portions. For sealing the housing interior, a sealing ring is inserted between the bead and the one housing portion, whereas at the opposite side, the bead bears directly at the other housing portion. The drive motor, which is fixed by means of the fixedly clamped bead in its fixedly determined position, is, however, rigidly mounted, so that the motor vibrations can be transmitted to the housing. Also, the relatively thin sealing ring is capable of changing very little as to these conditions.

SUMMARY AND OBJECTS OF THE INVENTION

The present invention therefore strives to overcome such drawbacks. It is thus an object of the present invention to provide a functionally positive, convenient to handle, tooth cleaning apparatus of the previously mentioned type, requiring virtually no maintenance, and which additionally can be assembled in a simple and time-saving manner.

By means of the oscillation dampening element which is fixedly retained in the housing, just as was the case for the last-mentioned prior art solution, the position of the drive motor within the housing is exactly fixed. Moreover, the motor is fixed in this position. However, the oscillation dampening element affords the additional advantage that the vibrations of the motor are not or are only to a limited degree transmitted to the housing. Hence, the operating comfort is increased. The vibration dampening element can additionally be constructed as a sealing element, which, with the vibration dampening element fixedly clamp between both of the housing portions, makes possible simultaneous sealing of the separation joint present between the housing portions.

A particularly simple assembly is then especially possible when both of the housing portions are connected with one another by means of a snap connection. This snap connection is preferably formed by cams at one housing portion and latching noses engaging therebehind at the other housing portion. By virtue of the vibration dampening element which is fixedly clamped between the housing portions, the parts of the snap connection are biased towards one another. Nonetheless, it is still possible to separate the housing portions from one another by releasing such snap connection without destroying the vibration dampening element, in the event repair work is needed to exchange elements arranged within the housing.

The assembly of the tooth cleaning apparatus is further simplified if at least the motor and, possibly, further components, are secured at a support element at which the ring-shaped vibration dampening element is mounted arranged in a circumferential groove.

If, as is known, a magnetically actuatable switch is mounted internally of the housing for turning-on and turning-off the drive motor, which switch can be opened and closed by a magnet element which is arranged at an actuation element displaceably guided at the outside of the housing then, two stops may preferably be arranged at the housing exterior or at the actuation element for the releasable arresting of the actuation element in the end positions. These stops can be travelled over and at the actuation element or at the housing exterior, respectively, by a latching element which coacts with the stops. Advantageously, the stops are formed by a web arranged at one housing portion and extending in the displacement direction of the actuation element, this web being engaged in both end positions of the actuation element by the latching element mounted at the latter.

In the description to follow there will be more fully explained, based upon the drawings, an exemplary embodiment of the subject matter of the invention.

DETAILED DESCRIPTION OF THE PREFERRED EMBODIMENTS

Figure 1:
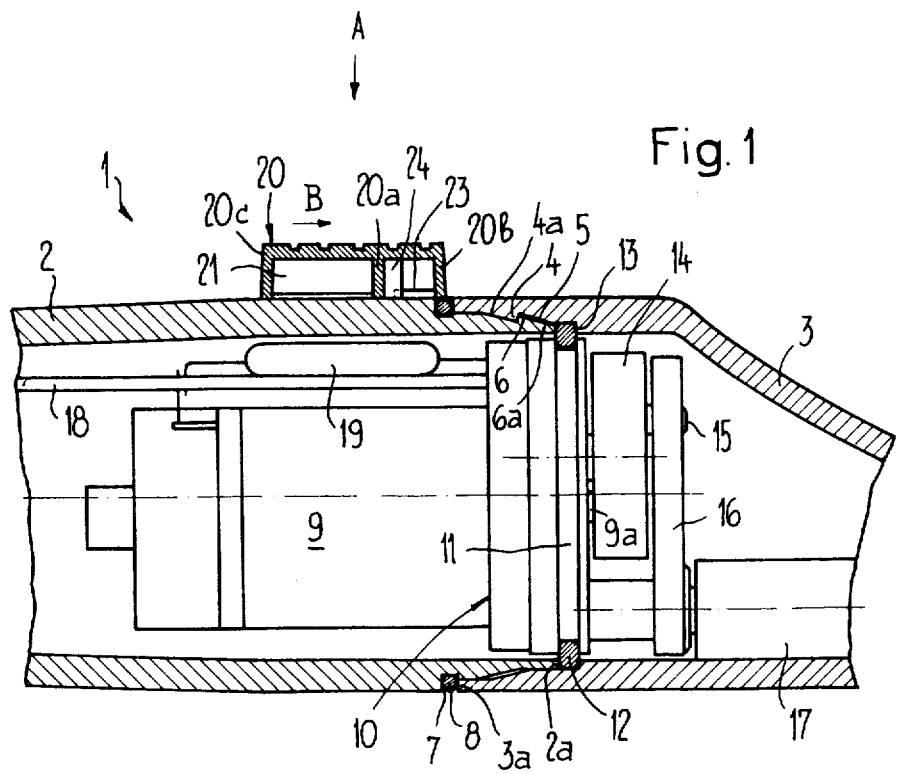
FIG. 1 a longitudinal sectional view through a part of the tooth cleaning apparatus of the present invention.

FIG. 1 shows in longitudinal section a part of an electrically operated tooth brush, which has a housing 1 composed of a rear housing portion 2 serving as a handgrip and a front housing portion 3. Both of the housing portions 2 and 3, which may preferably consist of a plastic material, are interconnected with one another by means of a snap connection. For this purpose, latching noses 4 are arranged at the inner side of the housing portion 3 and are distributed along the circumference thereof. The latching noses 4 are formed by undercut portions 5 in the housing portion 3. These latching noses 4 engage behind cams 6 which are provided at the outer surface of the other housing portion 2 and distributed in its circumferential direction. With the illustrated embodiment, three latching noses 4 and cams 6, respectively, for example, are provided. They are offset in each case with respect to one another through 120° in the circumferential direction of the corresponding housing portion 2 and 3, respectively. Both the latching noses 4 as well as the cams 6, exhibit inclined extending run-on surfaces 4a and 6a, respectively, for the associated cam 6 and the associated latching nose 4. In spaced relation from the cams 6, a groove 7 extends at the outer side of the rear housing portion 2, in which groove a sealing ring 8 is arranged, for instance an O-ring. The lower edge 3a of the front housing portion 3, with the housing portions 2 and 3 assembled together, presses, as illustrated, upon such sealing ring 8, so that it is somewhat compressed together between this edge 3a and the boundary walls of the grooves 7, in order to develop a faultless sealing action.

Internally of the housing, an electrical drive motor 9 is mounted which is secured to an essentially cylindrical support element 10. This support element 10 is provided with a ring groove in which there is inserted a ring 12 formed of an elastic material, preferably an O-ring. As illustrated in FIG. 1, this ring 12, with the housing portions 2, 3 assembled together, is pressed together between the edge 2a of the rear housing portion 2 and a shoulder 13 in the housing portion 3. This results, on the one hand, in fixedly clamping the support element 10 together with the drive motor in its position. Additionally, it sealing of the housing interior towards the outside. Moreover, this ring 12 has a vibration dampening action, so that the vibrations caused by the drive motor 9 are not or are only to an extremely limited degree transmitted to the housing 1 and to the hand of the user holding such housing.

Seated upon the motor shaft 9a is a gear which is not visible in FIG. 1, which meshes with a gear 14 having internal teeth and is rotatably mounted upon the support element 10. This gear 14 possesses an eccentrically mounted pin 15 which engages in a lengthwise groove of a rocker lever 16. This rocker lever 16 is rigidly connected for rotation with a tooth brush carrier 17, which, in known manner, extends past the front housing portion 3 and carries at its free end a tooth brush (not shown). If the drive motor 9 is placed into operation, then the rocker lever 16 is placed into a rocking movement by means of the gear 14 and the pin 15, which movement is transmitted by means of the tooth brush support 17 to the tooth brush.

At the support element 10 there likewise is attached a printed circuit board 18 which carries the elements needed for the operation of the drive motor 9. At this printed circuit board 18 there is also connected an infeed cable which has not been shown in FIG. 1 and which is sealingly guided through the rear housing portion 2, which cable can be connected with an electrical power source, for instance an outlet. Only magnetic switch 19, which is preferably a reed switch, has been shown mounted upon such circuit board 18 in FIG. 1. By means of this switch 19, drive motor 9 there is turned-on and off. The switch 19 is of known construction and possesses two contacts (not shown) which can be activated by a magnetic element 21 which is mounted in an actuation element 20 arranged at the outer side of the housing portion 2. An electrical tooth cleaning apparatus having such type magnetic switch is known basically from Swiss Patent No. 459,142. With this known solution, such switch is attached to the inner housing wall, whereas with the inventive tooth cleaning apparatus, the magnetic switch 19 is attached to the circuit board 18, as shown in FIG. 1. Due to this measure, the assembly of the switch 19 is appreciably simplified in relation to the aforementioned known solution.

The actuation element 20 is constructed as a slide which can be displaced in the direction of the arrow B out of its cut-off position, shown in the Figures, into a cut-on position, where both of the contacts of the switch 19 are closed in a known manner by the magnet element 21. The internally extensively hollow actuation element 20, which is open in the direction of the housing portion 2, possesses a ring or rectangular-shaped wall 20a which defines a receiving chamber for the magnet element 21, as such will particularly be evident from FIG. 2, in which there has been shown in cutaway view a part of the ceiling wall of the actuation element 20.

For guiding the actuation element 20 in the lengthwise direction, two guide rails 22 are arranged at the rear housing portion 2. They are arranged in spaced relationship from one another and extend in the displacement direction B of the actuation element 20, of which in FIG. 2 only one of them has been shown. Each of these guide rails 22 has a ledge engaging therebelow which is not visible in the Figures. A ledge is mounted at the inside of each side wall 20d of the actuation element 20, so that the actuation element 20 is retaind at the guide rails 22 and can be displaced along the same. These ledges, together with the guide rails 22, form a snap connection. This snap connection enables, during assembly of the device, bringing the actuation element 20, by the action of pressure, into engagement with the guide rails 22. Both of the guide rails 22 additionally serve as stationary path limiting stops for the actuation element 20. In the cut-off position of the actuation element 20, illustrated in the Figures, the front wall 20b of the slide 20 bears at the front end surface 22a of the guide rails 22, as the same has been shown in FIG. 2. If the actuation element 20 is moved in the direction of the arrow B in its cut-on position, then this movement is limited since the rear wall 20c of the actuation element 20 impacts against the rear end surface 22b of the guide rails 22.

Figure 2:
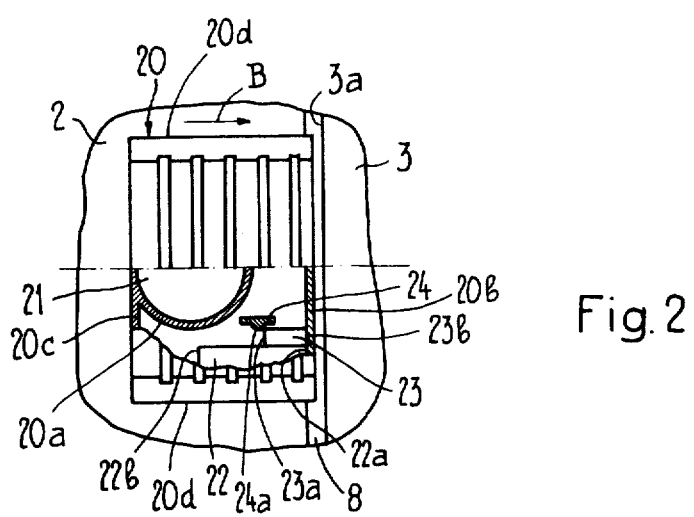
FIG. 2 is a top plan view of the region of the actuation element in the direction of the arrow A of FIG. 1.

For the releasable arresting of the actuation element 20 in each of its end positions two webs 23 are mounted in neighboring relationship to the guide rails 22 at the rear housing portion 2, of which in FIG. 1 one web has been illustrated and the other in FIG. 2. Both of the oppositely situated end surfaces 23a and 23b act as travel-over stops for a latching element 24 which extends downwardly from the ceiling of the actuation element 20. Each of both latching elements 24 is provided with a projection, with which the latching element 24 in each end position of the actuation element 20 engages behind the related web 23, wherein the projection 24a bears against the end surface 23a or 23b, respectively, of the web 23. The latching elements 24 are elastically deformable, so that during performance of a displacement movement at the actuationelement 20, the latching elements 24 elastically bend-out and enable a displacement of the actuation element 20. As soon as the actuation element has reached its other end position, the latching elements 24 return back into their rest position, in which—as already mentioned—the projections 24a engage behind the webs 23. Thus, in a simple manner, the displacement path of the actuation element 20 is limited and the actuation element 20 is releasably arrested in each of its end positions.

The described tooth cleaning apparatus can be assembled in a simple manner. The support element 10, to which the drive motor 9 and the circuit board 18 with the remaining components as well as the gear 14 are attached, is mounted with the ring 20 upon the edge 2a of the rear housing portion 2. Thereafter, the front housing portion 3, in which the tooth brush support 17 and the rocker lever 16 are mounted, are shifted onto the rear housing portion 2, whereby the latching noses 4 together with their run-on surfaces 4a travel onto the run-on surfaces 6a of the cam 6. This results in an elastic deformation of the marginal region of the housing portion 3 and/or the housing portion 2. If the front housing portion 3 has been completely mounted, then the latching noses 4 engage behind the cams 6, whereby a faultless connection is obtained between both of the housing portions 2 and 3. Additionally, the ring 12 formed of elastic material and also the sealing ring 8 are compressed together, so that a faultless sealing of the housing interior is realized towards the outside. Finally, the actuation element 20 is pressed onto the rear housing portion 2.

Since the housing 1 possesses no recesses which could collect contaminants at its outer surface, maintaining the cleanliness of the described tooth cleaning apparatus can be accomplished without any effort, even at the region of the actuation element 20. By virtue of both seals 8 and 12, the penetration of water or other foreign bodies into the housing interior is faultlessly prevented. Since it is not difficult to seal the throughpassages in both housing portions 2 and 3 for the actuation switch for the motor 9, there is thus insured a tight closure of the housing.

The snap connection between both of the housing portions 2 and 3 enables opening the housing 1, so that a repair or an exchange of the components mounted within the housing interior is possible, without the housing 1 or the sealing ring 12 having to be destroyed.

I claim:

1. An electrical tooth cleaning apparatus, comprising:
    a housing composed of at least two mutually interconnected housing portions;
    a drive motor arranged in said housing;
    a support for a tooth brush arranged to be driven by said drive motor;
    a vibration dampening element fixedly clamped between both of said housing portions;
    said drive motor is mounted in said housing and is fixed in position by means of said vibration dampening element;
    a snap connection for interconnecting both of said housing portions with one another; and
    said snap connection is constituted by cooperating connecting elements provided on each of said housing portions.

2. The tooth cleaning apparatus according to claim 1, wherein the vibration dampening element is further constructed as a sealing element.

3. The tooth cleaning apparatus according to claim 1, wherein the vibration dampening element is a ring formed of elastic material.

4. The tooth cleaning apparatus according to claim 3, further including a support element mounted in said housing to which the motor is secured, and at which the vibration dampening element is mounted.

5. The tooth cleaning apparatus according to claim 4, further including a groove at the circumference of said support element into which said ring-shaped vibration dampening element is inserted.

6. The tooth cleaning apparatus according to claim 3, wherein said ring is an O-ring.

7. The tooth cleaning apparatus according to claim 4, further including printed circuit board means and gear means attached to said support element.

8. The tooth cleaning apparatus according to claim 1 wherein said cooperating connecting elements are formed by cams provided at a housing portion and latching noses provided at the other housing portion which engage said cams.

9. The tooth cleaning apparatus according to claim 1, further including a magnetically actuatable switch mounted internally of the housing for switching-on and switching-off the drive motor, a magnetic element arranged at an actuation element displaceably guided at the outside of the housing for opening and closing said switch, two stops arranged at the housing outer surface or at the actuation element for the releasable arresting of the actuation element in its end positions, said stops being capable of being travelled-over, and a latching element which coacts with such stops.

10. The tooth cleaning apparatus according to claim 9, wherein the stops and/or the latching element are elastically deformable.

11. The tooth cleaning apparatus according to one of the claims 9 or 10, wherein the stops are formed by a web arranged at one housing portion and extending in a displacement direction of the actuation element, which web engages in both end positions of the actuation element behind latching elements mounted at the actuation element.

12. The tooth cleaning apparatus according to claims 9 or 10, wherein the actuation element is connected by means of a snap connection with the housing.

13. The tooth cleaning apparatus according to claim 12, wherein the actuation element has two side walls for engaging below a guide rail mounted at one housing portion and is guided in lengthwise direction by said guide rail.

14. The tooth cleaning apparatus according to claim 13, wherein each guide rail serves as a fixed displacement limiting stop for the actuation element.

15. The tooth cleaning apparatus according to claims 4 or 9, characterized by the features that the switch is mounted upon a printed circuit board secured at the support element.

* * * * *